United States Patent
Shay et al.

(10) Patent No.: US 8,834,411 B2
(45) Date of Patent: Sep. 16, 2014

(54) MEDICAL DEVICES FOR DISPENSING POWDERS

(75) Inventors: Christopher D. Shay, Horseshoe Bay, TX (US); Timothy R. Sullivan, Austin, TX (US)

(73) Assignee: Mystic Pharmaceuticals, Inc., Austin, TX (US)

( * ) Notice: Subject to any disclaimer, the term of this patent is extended or adjusted under 35 U.S.C. 154(b) by 44 days.

(21) Appl. No.: 13/433,586

(22) Filed: Mar. 29, 2012

(65) Prior Publication Data

US 2012/0259277 A1   Oct. 11, 2012

Related U.S. Application Data

(60) Provisional application No. 61/472,341, filed on Apr. 6, 2011.

(51) Int. Cl.
*A61M 11/00* (2006.01)
*A61M 15/00* (2006.01)
*A61M 35/00* (2006.01)
*A61M 25/00* (2006.01)
*A61M 11/02* (2006.01)

(52) U.S. Cl.
CPC ......... *A61M 35/003* (2013.01); *A61M 15/0036* (2014.02); *A61M 25/0082* (2013.01); *A61M 2202/064* (2013.01); *A61M 11/02* (2013.01); *A61M 15/0028* (2013.01); *A61M 15/0041* (2014.02)
USPC ............................................. 604/58

(58) Field of Classification Search
USPC ................... 604/58–61, 63; 206/531–532
See application file for complete search history.

(56) References Cited

U.S. PATENT DOCUMENTS

| | | | |
|---|---|---|---|
| 5,270,305 A | 12/1993 | Palmer | |
| 5,590,645 A | 1/1997 | Davies et al. | |
| 5,655,523 A * | 8/1997 | Hodson et al. | ........... 128/203.15 |
| 5,860,419 A | 1/1999 | Davies et al. | |
| 5,873,360 A | 2/1999 | Davies et al. | |
| 6,032,666 A | 3/2000 | Davies et al. | |
| 6,142,146 A | 11/2000 | Abrams et al. | |
| 6,428,809 B1 | 8/2002 | Abrams et al. | |
| 7,669,597 B2 * | 3/2010 | Sullivan et al. | ........... 128/203.21 |
| 7,950,390 B2 | 5/2011 | Gumaste | |

* cited by examiner

*Primary Examiner* — Nicholas Lucchesi
*Assistant Examiner* — Melissa A Snyder

(57) ABSTRACT

A medical device for topical, intranasal or oral administration of dry powder medical compositions includes a unit dose blister form containing an internal piercing device that provides for agitation, dispersion and dispensation of the powder to a user.

11 Claims, 6 Drawing Sheets

MEDICAL DEVICES FOR DISPENSING POWDERS

CROSS-REFERENCE TO RELATED APPLICATIONS

This application claims benefit of priority to U.S. Provisional Application 61/472,341 filed Apr. 6, 2011, the disclosure of which is incorporated herein by reference for all purposes.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The present invention is in the technical field of medical devices. More particularly, the present invention is in the technical field of medical devices for the administration of drugs, medical compounds, and pharmaceuticals as powders orally or intra-nasally to a user.

BACKGROUND OF THE INVENTION

Certain diseases and medical conditions that are either systemic or local to the respiratory tract are treatable via the administration of drugs and therapeutic agents taken orally or nasally. There are a growing number of drugs that are most effectively manufactured, stored, delivered, and administered as a dry powder formulation. A number of pharmaceutical agents are deliverable as powders or particles orally or intra-nasally, including but not limited to antibiotics, antipyretics, anti-inflammatories, biologics, vitamins, botanicals, co-factors, enzymes, inhibitors, activators, nutrients, vaccines including DNA based killed or live virus or microorganisms, nucleic acids, proteins, peptides, antibodies, peptide mimetics, prophylactic or therapeutic anti-viral and anti-bacterial compounds and biologics, and other agents or pharmaceutical compositions.

Solid formulated pharmaceuticals have a number of recognized advantages. Compound stability for certain agents is greater in solid form especially polypeptide and protein based biologics whose conformational and higher structure may tend to degrade or denature when in solution thus affecting their biological activity. Similarly, certain drug chemical compounds may tend to dissociate and degrade due to incremental pH shifts, Van der Waals and other forces resulting in diminished shelf life and drug efficacy. Consequently, unstable drug compounds formulated as liquids must be refrigerated or even frozen to preserve their effectiveness which adds cost and complicates deployment. This is especially troublesome in such cases whereby vaccines and other unstable drugs are needed to be distributed to remote areas and underdeveloped regions. Often unstable drugs must then be shipped in solid form and reconstituted back to liquid form at the time of administration thus adding expense and the need for skilled personnel for proper utilization.

In certain other cases medications are designed in solid form to facilitate controlled release to result in sustained pharmacological concentrations of active ingredients over an extended period of time. For systemic treatments, powder based drugs delivered either intranasally or orally offer a number of advantages including rapid drug uptake due to large area pulmonary deposition, the avoidance of the harsh environment of the stomach and intestinal tract as in the case of pills, tablets, and capsules, and the avoidance of broad systemic and side effects often associated with parenterally administered drugs. Other advantages include enhanced bio-availability, reduced dose volume, and improved patient compliance and ease of self-administration.

Typically these agents and medicaments are formulated and prepared from solution by recrystallization followed by milling, but for improved control over particle crystallinity, shape, mean size, and size distribution; lyophilization or various spray drying techniques know in the art are relied upon to produce a bulk powder with precise characteristics to aid in administration. Key characteristics include primarily the mean particle size as well as the distribution of sizes within the bulk powder. For a given inspiratory velocity initiated either nasally or orally, a certain mean particle size and mass is required to result in deposition to the targeted tissue location within the targeted area within the respiratory tract. Generally, smaller particles will tend to deposit deeper in the respiratory tract, more particularly; particles of 3 or fewer microns in diameter have a greater probability to reach the tissues of the lower lungs, with even smaller aerodynamic diameters preferred for enhanced systemic uptake. Conversely, larger particles of greater than 5 microns to the tens of microns or larger, owing to their larger mass are more likely to deposit proximally to the point of administration; most typically within the nasal cavity and passages when administered intranasally, or in the oral cavity or pharynx, larynx, or trachea if orally administered. The dispersity or polydispersity index describes the range and proportion of sizes within the bulk powder. Depending upon the targeted application location, a less disperse or mono-disperse powder may be desired to assure a specific deposition location or a more disperse powder may be necessary in order to impact a larger range of tissues such as the case with certain anti-viral therapies and vaccines where the intent is to contact the virus residing in several tissue areas and locations with the respiratory tract. Other aspects of powder engineering are intended to impact the flowability and reduce the aggregation of the powders in order to aid in the friability of the material to increase the delivery efficiency, efficacy and rate of uptake. For that reason, certain excipients, carriers, or other matrix components may be added in defined quantity to the active dry pharmaceutical agent to impact particle shape, texture and surface properties for reduced adhesive and electrostatic forces in order to facilitate the breaking apart of settled or aggregated particles prior to and during dispense. Further, micro and nano particle formulations of drugs are often employed using biocompatible and degradable polymers as carriers.

All of these and other powder engineering principles play an important role in conjunction with the design of packaging and dispensing devices to achieve precise delivery of powdered drugs. A variety of packaging and devices are known for delivering a controlled quantity of a dry pharmaceutical preparation to the nose, nasal mucosa, sublingual, buccal, oral mucosa, pharyngeal, tracheal, and lower respiratory tissues.

Unlike liquid drug formulations, whereby a simple pump can deliver a precisely controlled quantity of drug as droplets with the required spray characteristics; drugs formulated as dry materials present additional challenges owing to the propensity of powders to settle and physically and chemically agglomerate. Thus it is necessary that the device must not only contain a single dose of material or be capable of metering it from a bulk source, but must also impart sufficient energy to agitate the material to break up the particles and propel them to the user in the correct quantity and mean particle size in order to provide optimum deposition characteristics, and consequently the most advantageous therapeutic effect.

There exists numerous means and devices to dispense powders to a user; the basic designs of which vary depending upon the site of administration and the target deposition zone within the respiratory tract. For example, Dry Powder Inhalers (DPIs) is the class of devices that is perhaps the most common type of device for delivering dry pharmaceutical preparations to a user most typically for pulmonary deposition via oral administration. Typically such devices require an external propellant, pressurizer or other external energy source which classified those devices generally as Active Dry Powder Inhalers (ADPIs). Alternatively, other devices rely solely on the inspiratory airflow of the user and hence are breath actuated and referred to as Passive Dry Powder Inhalers (PDPIs). Both approaches suffer from significant drawbacks. In the case of ADPIs, owing to the need for a propellant or electromechanical componentry and often bulk storage of drug; the device itself can be complex, large, expensive, cumbersome, and inconvenient to handle and use. Passive devices while often smaller, less expensive and containing one or more individualized unit doses; often deliver inconsistent quantity of drug to the user with the variability of delivered dose a function of user inspiratory flowrate. Further, the passive devices often operate at a reduced efficiency as given by the fraction of the dose quantity actually delivered to the user. The reduced efficiency diminishes the cost effectiveness of the passive devices due to wasted drug material. The undispensed portion of the drug that remains is also left behind to contaminate the device, and in the case of multi-dose devices, possibly contaminate subsequent doses of drug.

In the case of pulmonary deposition, very small particles (1-5 microns) are preferred but smaller particles typically suffer from an increased tendency to form clumps due to hygroscopicity, adhesive and electrostatic forces. Prior art devices commonly rely on high velocity propellants or electromechanical agitation to de-aggregate the powder particles and deliver the material to the target deposition zone of the user. The means of providing the external energy source are widely varied and include pressurized canisters, propeller type agitators, mechanical, solenoid or piezoelectric based vibration to aid in particle deaggregation and delivery. For example, Gumaste in U.S. Pat. No. 7,950,390 discloses a microelectronic piezo vibrator to aid breaking apart the agglomerated particles and suspending them into the flow field. Such microelectronic systems offer improvements in the bulk size of the device as compared to Wilke et al, who in U.S. Pat. No. 3,948,264 discloses a battery driven electromechanical vibrator to facilitate dispersion and release of the particles. These schemes, while incrementally different, consistently suffer from the disadvantage of system complexity due to the need for circuitry, motors, and electrical power sourcing. Additionally, these prior art types of devices often entail capsule based dosage forms externally pierced by various means often including retractable mechanical or motor driven pins, often arranged in multiple pin arrays and channels to facilitate increasing the fraction ejected from the dosage form.

Alternatively, passive devices rely upon the forceful inhalation of the user to disperse the particles and deliver them to the airway and the targeted tissues. In most prior art, active and passive devices, the operation often entails a series of steps to facilitate administration of drug. Additionally, the dosage forms are often singulated in the form of capsules containing the prescribed dose quantity that must first be externally pierced in order to expose the compound to the velocity field. The other dosage form common in such devices are individual blisters either singulated or in strips or cartridges that are loaded into the dispensing device and also first require either piercing of the blister or peeling of the upper lidding layer to expose the contents. For example, Davies et al in U.S. Pat. Nos. 5,590,645; 5,860,419; 5,873,360; 6,032,666 discloses an inhalation device with a multi-dosage configuration in the form of a strip of individual blisters containing the medicament. The base and lid materials are peeled apart as the strip is rotated into an opening station position and the two ends taken up on separate spools. Once in position and the contents exposed, the user then inhales the drug compound. This prior art device has the advantage of simplicity owing to the reliance upon the users inhalation as the primary means of particle dispersion and delivery. However, that approach may result in poor dose consistency; as measured by patient to patient variability or dose to dose variability of an individual patient. This variability is a consequence of the natural range of possible patient inspiratory rates and velocities. Further, the passive scheme as disclosed whereby no means are provided to augment the ejection of the blisters, may result in incomplete dosing and low efficiency of delivery whereby medication is left in the blister. Further, the undelivered quantity continues to reside within the opened blister and once indexed may fall out into the device interior, contaminating both the device and possibly subsequent doses.

Often such prior art devices incorporate various aspects on the exterior of the dosage form or in the device itself such as channels, variously configured inlets, outlets, and orifices or other turbulence promoting means for improving the dispersion of the particles. However, most such schemes result in modest improvement in dose efficiency.

The present invention addresses these disadvantages in the prior art devices by providing for a dosage form that is internally pierced using the user's own force. The internal piercing mechanism also provides agitation and pressurization of the blister form to impart velocity to the particles to break apart settled and agglomerated material and produce an inspiratory flowrate independent dosing. The combined dosage form and device can be single or multi dose capable for either nasal or oral administration of a range of particle sizes. The dosage and device provides for improved patient ease of use owing to its compact size and simple design without the need for electrical circuits or power sources, low cost, and consistent, contamination free dosing of dry powder drug compounds.

Device technology has lagged current powder formulation and powder engineering capabilities such that the enhanced precision and effectiveness of new and existing powdered drugs can be fully harnessed. The present disclosure provides dosage forms with integrated dispense energetics for delivery of predetermined quantities of dry powder or granular pharmaceutical or medical compositions for local and/or systemic action. Integrating the device energetics into the dosage form reduces overall device cost, complexity, and bulk to improve patient compliance and ease of use.

SUMMARY OF THE INVENTION

The present invention provides dosage forms with internal componentry which provides for piercing or opening of the form from the inside, mechanical agitation of the drug contents, and to aid in dispersion and dispensing of the drug to a user. The dosage forms may be in certain embodiments a biologic, a biological agent, or a small or large molecule pharmaceutical drug compound. The drug dosage forms are for use in delivery devices that deliver the drug compound as a dry powder, particles, granules or other agent or formulation as a dry material to a human or non-human animal. The dosage forms can be used, for example, to deliver one or more measured doses of a dry pharmaceutical, biologic or medical composition to the nose, nasal passages, mouth, throat, trachea, pharynx, upper or lower airways to include into the lungs, or to a topical location of a user for the therapeutic or prophylactic treatment of local or systemic conditions.

Any powder or dry form pharmaceutical is contemplated in the present disclosure, including but not limited to antibiotics, antipyretics, anti-inflammatories, biologics, vitamins, co-factors, enzymes, inhibitors, activators, nutrients, aptamers, thioaptamers, vaccines including killed or live virus or microorganisms, nucleic acids, proteins, peptides, antibodies, peptide mimetics, micro or nanoparticles, or other agents known in the art. The following is a limited list of examples of general classes of pulmonary drugs administered as inhalable dry powders for a host of indications which can include but not limited to anemia, asthma, bronchitis, cancer, cystic fibrosis, diabetes, osteoporosis, hepatitis, arthritis, chronic or acute pain, immunodeficiency disorders, multiple sclerosis, endocrinological disorders, etc. Drug compounds for treating those indications include, various adjuvants, calcitonin, erythropoietin, heparin, inhibitors, insulin, interferons, interleukins, hormones, neurotropic agents, growth factors, stimulating factors, vasodilators and constrictors, etc. This list is not intended to be exhaustive and in no way is inclusive of all possible conditions and diseases, drugs and compounds, or routes or targets of administration, but rather is to illustrate the breadth of dry powder drugs and indications employable in the present invention and contemplated by the present disclosure.

In certain embodiments, the medical compositions are in the form a powder, or a dry pharmaceutical combined with one or more active agents and combinations of pharmaceutically acceptable carriers or materials to include matrix agents, diluents, preservatives, coatings, adsorption or absorption enhancing or delaying agents, salts, bulking or filling agents, anti-clumping agents, adjuvants, buffers, chelators, or other excipient ingredients known to those in the art as needed to affect the drug's stability, flowability, adhesion, dispersion and deaggregation characteristics, or pharmacological uptake, efficacy, activity and rate of release. For example, in certain embodiments a predetermined quantity of biological or pharmaceutical material may be combined with mannose, lactose or other carrier or bulking agents known in the art. The drug may also be bound to or encapsulated within nanoparticles or other macromolecules to aid in stabilizing the drug and/or affecting the drug compound's rate of release over time. Any conventional media or agent compatible with the active agent is contemplated. More than one active agent may also be incorporated into the compositions, for the same or separate purposes. The phrase "pharmaceutically acceptable" refers to compounds and compositions that are appropriate for human or non-human animal use and do not otherwise produce an allergic or other undesired reaction or effect when administered to a human or animal.

The present disclosure addresses the inherent disadvantages of prior art dry powder delivery dosage forms and devices. The present invention provides crushable dosage forms that contain the dry powder as well as an internal piercing device that opens the dosage form and agitates the drug to break apart the particles and disperse them to the user. Various devices within the prior art include measured quantities of dry powdered formulations and pharmaceutical compositions contained in a crushable ampoule, blister or other dosage form that entail forcing the form against an eternal piercing device during use, in order to pierce the dosage form and release the contents. The inherent disadvantages involve the reliance on external energy sources and/or solely upon the inhalation force of the user to adequately break apart the settled and aggregated dose material into individual particles. The present invention provides for piercing the dosage form from the inside whereby that piercing device and piercing event agitate the form contents to break up the material, and deliver the dry powder to the user. In the present invention, the energy source for particle break up, dispersion, and delivery is provided by the user's hand force during the mechanical actuation of the device. In certain embodiments the user driven device actuation force may be combined with or augmented by additional external energy supplying means and devices and contemplated herein.

In certain embodiments the crushable unit dosage forms of the present disclosure are blisters that can be manufactured as described by Nelson in U.S. Pat. No. 7,963,089 and incorporated in its entirety herein by reference. The manufacturing processes for forming blister wells for unit-dose packaging in a continuous web can include a step of drawing a metal, polymer, or laminated metal-polymer foil or other suitable sheet of material with the appropriate mechanical characteristics to allow hot or cold forming and drawing known in the art. In certain embodiments, one or more plungers can be used to form a primary contour, the contour having a depth of at least 100% and up to 150% of the depth of the final formed recess or well. A second stage involves shaping the primary contour with one or more of the same or additional plunger(s) to the desired formed recess depth and shape, with a depth that is less than the depth of the primary contour, while substantially maintaining the surface area of the primary contour formed in the first stage. The contour or shape of the blister well can be formed to contain certain shape features, indentations, or be imparted with texture by the forming pins to provide for a means of securing the internal piercing device within the blister well or recess. The formed well or recess is then loaded aseptically with the predetermined quantity of sterile dry powder and the internal piercing device and a lidding material of the same or similar laminated material as the blister well or other sheeting material can be rolled atop the recesses and bonded to the well sheeting with adhesives, or by thermal or ultrasonic or other welding means. The mass and volume of particles dispensed from an individual blister are various depending upon the blister shape and volume, the required volume of headspace gas, and the powder characteristics, which are primarily the bulk density which is affected by the particle shape, size, and adhesion and aggregation properties, among others. For example, the dosage mass and volume for intranasal or orally administered pulmonary treatments can range from 1 to 50 milligrams and 10 to 100 microliters, respectively. This is but a single typical range for one application; ranges for other indications and routes of administration and needed therapeutic quantities can vary substantially and are contemplated herein to include ranges to gram level masses and 1000 microliters dose volume or more for certain topical administered compounds.

In certain embodiments, the individual blisters that can be formed in sheets are in later manufacturing steps, singulated into single doses for use in single-use, disposable, non-reloadable devices, or for use in devices which are reloadable with additional unit doses for subsequent dosing of the same or different patient(s). Alternatively, and depending upon the application and indication, the sheets may be formed and cut into rows, arrays, grids or other configurations of blisters suitable for use in multi-dose devices. Regardless of the shape, size, or geometric configuration of blisters, ampoules, or wells; each unit contains an internal piercing element.

Preferred embodiments of the present invention can provide dosage forms containing a piercing device that pierces the blister from the inside, mechanically agitates the dry powder, disperses, and dispenses the blister contents from the blister to the user.

The internal piercing device can include a lower section that is a circular ring, a disk, or has a concave shape, and a hollow tip that is an elongated member extending from the lower section. The ring can be narrow, flat or tubular in shape and stabilizes the internal piercing device's position within the blister. The device can include connecting member splines, spokes, ribs of various shapes and numbers to connect the stabilizing ring to the hollow tip in order to provide for communication of the blister contents to the hollow tip's internal channel for dispensation of the powder. The hollow elongated tip can include additional orifices, channels, obstructions or other structural features to affect agitation and turbulent flow within the blister and/or within the tip during piercing and dispensing of the dry powder.

In preferred embodiments, two, three or a plurality of the connecting legs or members can connect the ring element to the hollow elongated tip; the legs of which can be flat, circular, or curved or arch shaped; such that they form a substantially vacant interior cavity for the powder to reside and divide the powder to reduce caking and aid in dispersion.

In certain other embodiments, the base and leg members can be a mesh or porous material or a highly perforated disk that provides void spaces for deaggregation and to prevent or reduce caking or settling of the powder and to promote turbulence to aid in powder dispersion during dispense.

In certain embodiments, the hollow elongated tip can be of various shapes to include but limited to a parallel walled pipe to a tapered hollow cone. The internal channel can be of constant diameter, tapered, rifled or containing other structures to affect velocity, pressure, and turbulence. The inside diameter of the hollow elongated tip can range from about 0.01 to 0.1 inches depending upon the powder characteristics and puncture needs. For example, for a powder that is free flowing with a small mean diameter, with low homogeneous adhesivity, and low dose mass; where a quick, short puncture event is preferred, a thicker walled tip will better support a sharper tip, which hence permits a smaller interior diameter of the tip.

The total height of the internal device including the base and hollow elongated member is less than the internal height of the blister well at its center, but in certain other embodiments may be of slightly greater length to include the range of 110% or more of the inside height of the blister to provide for pre-stretching or pre-puncturing of the lidstock. The hollow tip end can be of blunt to sharp shape to facilitate or delay the piercing of the blister lidstock during the crush event to provide for variable internal pressurization prior to blister dispense to impart agitation and aid in deaggregation and dispersion. In summary, the internal piercing device's elongated tip, base and connecting leg members act in conjunction to divide the powder dose, promote turbulent mixing, and pressurization prior to and during dispensation of the powder from the blister.

In certain other embodiments, the piercing device can be described wherein the legs, splines, or spokes that connect the base section to the elongated hollow tip can be made thin such that when the blister is undergoing crushing, the piercing device collapses whereby the elongated tip moves downward and the base ring flips forward such that it acts as a mechanical spring the energy of which acts to provide agitation and deaggregation of the powder material.

In certain embodiments, therefore, the disclosure may also be described as a piercing device that acts to agitate and dispensing a predetermined quantity of solid composition from a dosage form. The piercing device includes an elongated hollow tip member with an inlet end and a discharge end, with the internal channel connecting the inlet end and the discharge end in fluid communication, a blunt or sharp shaped tip forming a discharge opening in the discharge end, and features on the internal chamber surface to control the pattern of powder forced through the piercing device such that it also acts as a nozzle. The disclosure includes, therefore, a dosage form that comprises the piercing device and a quantity of a dry powder pharmaceutical composition.

The internal piercing can be manufactured by techniques known by those skilled in the art, for example injection molding or machining. The piercing device can be constructed of any material with suitable chemical compatibility and mechanical properties to impart the designed for strength characteristics such as ceramic, glass, metal, plastics and in preferred embodiments, can be constructed from polymeric materials to include but not limited to polyethylene (PET), polypropylene, polystyrene, or poly ether ether ketone (PEEK), self-reinforced polyphenylene (SRP) or other pharmaceutical or medical grade materials. In preferred embodiments, the internal piercing devices are injection molded as single piece components, however in certain other embodiments where certain structural features are less amenable to one piece molding; the devices can be assembled from multiple machined and/or molded parts. For example, certain embodiments may entail attaching by snap or press fit or threading of a machined metal elongated tip to a plastic base part. Other combinations of parts, manufacturing methods, materials, and assembly methods are well known in the art and fully contemplated herein.

In certain preferred embodiments the present disclosure is a dosage from containing an internal piercing device as described herein. The dosage form can be a crushable blister or ampoule containing a powder medical composition. The blister well can be sized to permit sufficient volume to contain both the prescribed dose quantity of dry powder material loaded into the blister as well as a headspace of free gas volume that remains to permit pressurization and agitation of the contents. Such dosage forms are for use in delivery devices and systems in which a handheld device that includes an actuation mechanism that can include a ram, piston or plunger which when forced against the dosage form pressurizes the blister contents during the compression phase of the dispense that occurs prior to and during initial breaching or piercing of the lidstock by the internal piercing device. Once pierced, the pressurized and agitated contents are forced out through piercing device's elongated hollow tip internal channel.

The present disclosure provides a dosage form containing dry powder medical composition and an internal piercing device that provides the advantages of pressurization, agitation, dispersion integral to the blister owing to the internal piercing device which also acts as a nozzle to dispense the powder contents to the user without the requirement of an external energy source common with active devices known in the art and provides increased ejection fraction and hence greater efficiency of drug delivery above that as provided by passive devices.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

BRIEF DESCRIPTION OF THE DRAWINGS

The following drawings form part of the present specification and are intended to further demonstrate certain aspects and embodiments of the present invention. Reference to the drawings in combination with the detailed description is intended to further illustrate certain features of the internal piercing device in conjunction with the dry powder containing dosage form.

DETAILED DESCRIPTION OF THE PRESENT INVENTION

Preferred embodiments of the present disclosure provide dosage forms that contain a measured quantity of dry powder, a piercable section such that the dosage form can be pierced, an internal piercing device that pierces the piercable section, provides agitation and dispersion of the powder and communicates the powder to a user. When employed in a typical device, a plunger, lever, ram, wheel, or some other mechanical device contacts the dosage form with sufficient force to crush the dosage form to expel the powder contents out of the pierced opening. The dosage form can be generated using methods well known to those of skill in the art, including, for example, form fill seal technology or blow fill seal technology, or by deep draw forming as described in U.S. Application Publication No. 2009/0071108, incorporated herein in its entirety. The form-fill-seal process can be used to create a blister, for example a pack or strip of blisters, from rolls of flat sheet or film, filled with the dry powder pharmaceutically active agent, and closed or sealed on the same equipment. This process entails clamping the laminate or film material, pressing one or more forming pins through plates with appropriately sized and spaced openings to form the blister well or receptacle in which the pharmaceutically active agent, or an agent that may be mixed or combined with a pharmaceutically active agent is placed. The lidstock or lidding of the same or similar material is sealed across the blister well leaving a pierceable covering through which the agent is dispensed out of the blister.

Preferred embodiments of the present disclosure provide dosage forms for use in delivery devices for intranasal or oral administration of dry powder drugs or pharmaceutical compositions. A controlled quantity of dry material is contained in a blister form that also contains an internal piercing device. One or more sealed unit dose blisters are then loaded or mounted into a handheld device that allows a user to dispense the powder. When the blister is mechanically compressed or crushed by the device, the internal piercing device ruptures the blister, agitates and disperses the powder contents and provides a channel for the expulsion of the powder into the nose or mouth of a user.

Figure 1A:
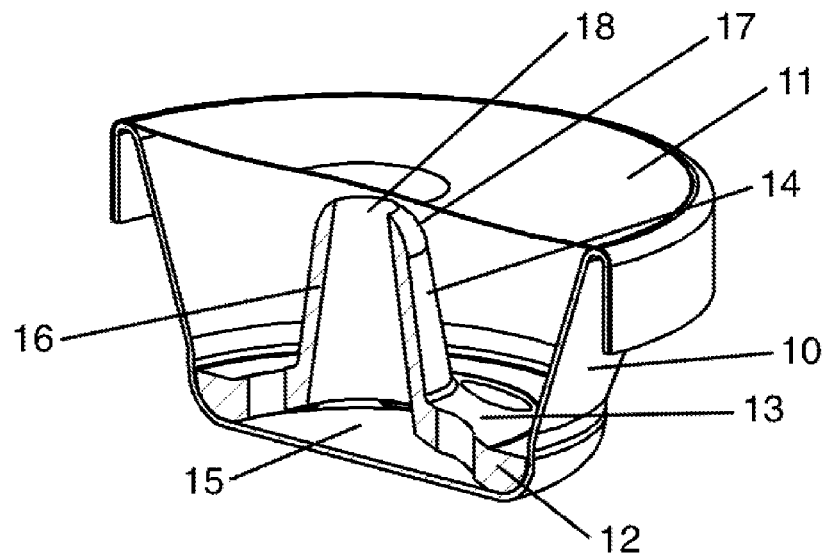
FIG. 1a is an embodiment showing a cutaway view of a unit dosage form of the present invention containing an internal piercing device with support members forming a cage-like structure and substantially free flow path.

FIG. 1A is a cutaway view of an example of a dosage form. The blister well or receptacle 10 is sealed by the lidding or lidstock material 11 to form a single unit dose blister. Contained within the closed blister is an internal piercing device with a base ring 12. Multiple support members 13 communicate with the hollow elongated tip 14. The channels form a substantially open, conical shaped volume 15 within the piercing device. The void volume is designed to promote free flow of the powder to the tip. The tip can be have tapered or straight walls 16, can be substantially smooth internally or contain structural features to aid in powder breakup, and can be blunt or sharp at the end 17 to facilitate or delay puncture. During dispense, the opening at the tip end 18 forms the discharge point for the powder which is delivered to the user.

Figure 1B:
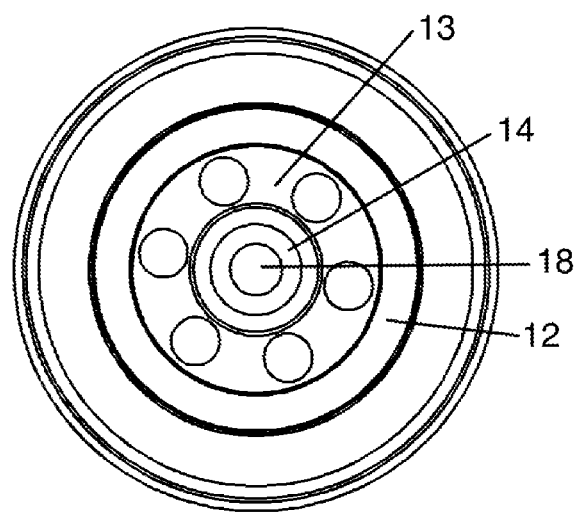
FIG. 1b is the same embodiment showing a top view of a unit dosage form of the present invention containing an internal piercing device.
Figure 2:
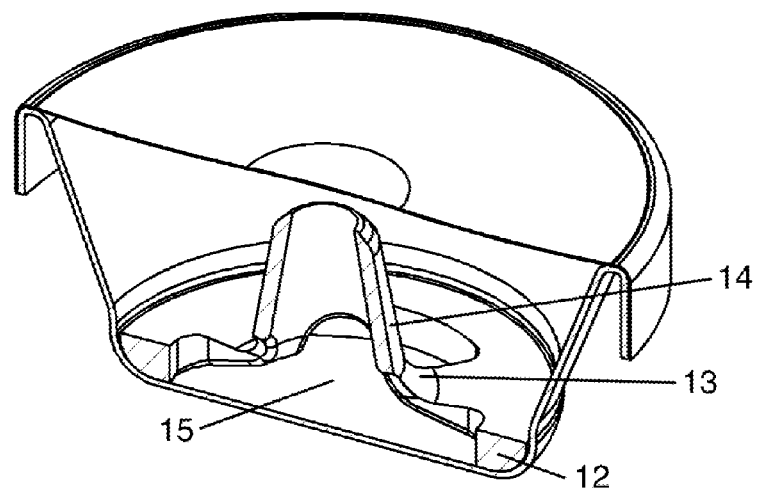
FIG. 2 is an embodiment of a dosage form with a high internal volume void cavity formed by three spokes or connecting members between the ring and hollow elongated tip.

FIG. 1B is a top down view of the same dosage form shown in FIG. 1A. In this view, the ring 12, support members 13, elongated tip 14, and the discharge opening 18 diameter are evident.

As discussed in the background section, those skilled in the art are familiar with the range of factors affecting the flow characteristics of dry powders as well as the powder engineering and formulation principles entailed in achieving a free flowing powder. The quantity of dry powder pharmaceutical contained in a dosage form nonetheless can settle, cake, and aggregate. The internal piercing devices as shown in FIG. 1A, 1B and FIG. 2A, 2B are designed to provide a high volume flow path for the powder. Rather than individual orifices and small channels, which in the case of powder dispensation would otherwise tend to plug or clog, the present invention provides embodiments that have a stabilizing ring 12 with several connecting legs or members 13 that connect the ring to the hollow elongated tip 14 thus providing a substantially freer or cleaner pathway for the powder to travel. In the various configurations, the connecting members can be, for example, arched to provide a concave center volume space 15 that gives a substantially open flow path for powder. Additionally, the number of connecting members can be few, e.g. one to three; or several, e.g. four or more, to divide the powder into individual segments within the blister during storage. During dispense, the individual segments of powder serve to break apart the powder thus providing for greater powder surface area exposure to the pressure that occurs during blister compression; further breaking apart the powder cake and propelling it into the piercer hollow elongated tip for discharge.

Figure 3:
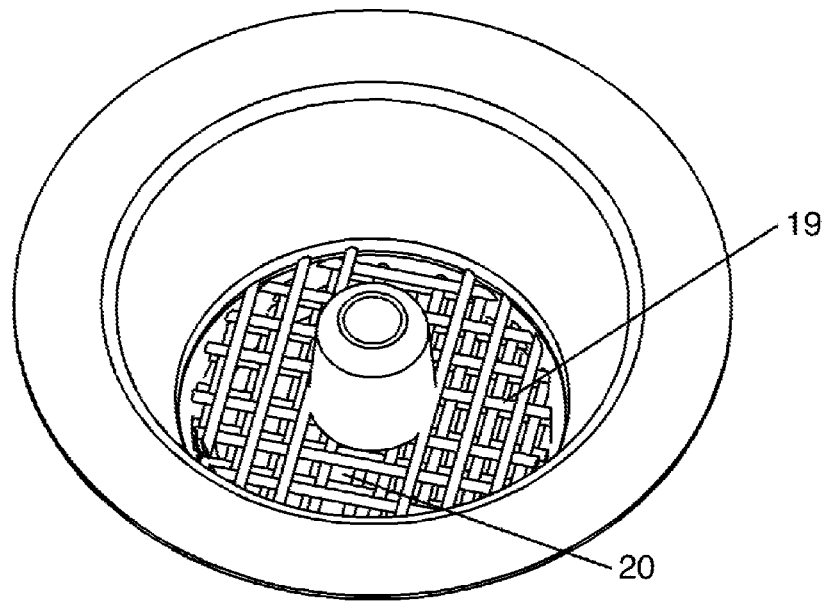
FIG. 3 is an embodiment of a dosage form with a mesh or highly porous base internal piercing device.

For even greater division of the powder dose contained within a dosage form, the internal piercing device embodiment of FIG. 3 provides a mesh or highly porous base 19. The base can be disk shaped or concave and attached to the elongated tip 14. In the case of a mesh base, the irregular segments of powder 20 act to increase turbulence in the pressure field acting upon the powder during blister compression and dispense.

Figure 4:
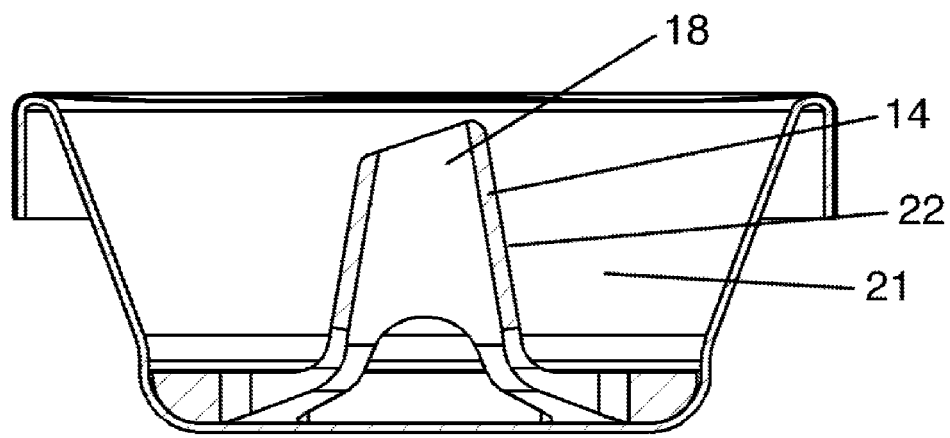
FIG. 4 is an embodiment of a dosage form with an internal piercing device with a tip modified to facilitate puncturing or piercing of the lidstock.

FIG. 4 is an embodiment demonstrating a tip modified to facilitate the piercing of the lidstock. The height of the elongated tip 14 and its bluntness or sharpness, the blister headspace volume 21, and lidstock tensile strength due to its composition and thickness combine to dictate the time and distance of travel that occurs during blister crushing before the piercing event occurs. These design parameters allow for optimization of the pressure to increase agitation, dispersion and velocity of the powder at discharge. Integral to blister pressurization is the smooth exterior wall 22 of the tip that provides a seal between the tip and the lidstock opening during piercing and discharge. The seal is advantageous to maintain the blister pressure and assure the powder is ejected through the tip's internal channel 18.

Figure 5A:
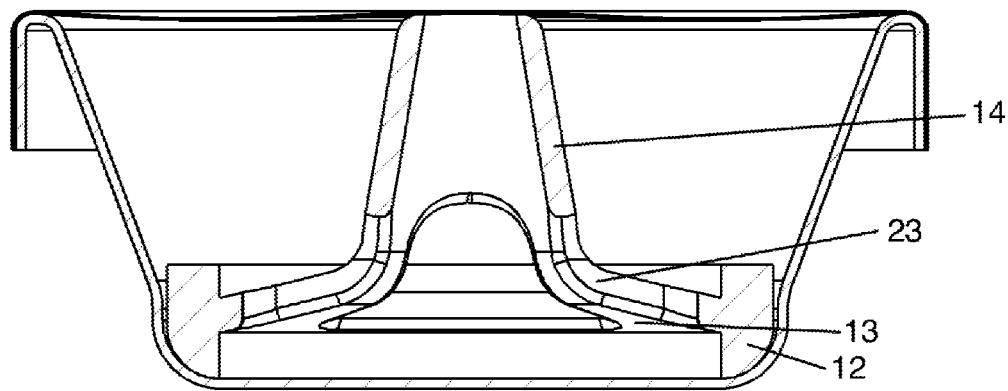
FIG. 5A is an embodiment of a dosage form with an internal piercing device that is collapsible and acts as a mechanical energy storage device that springs forward to aid in powder agitation and breakup.
Figure 5B:
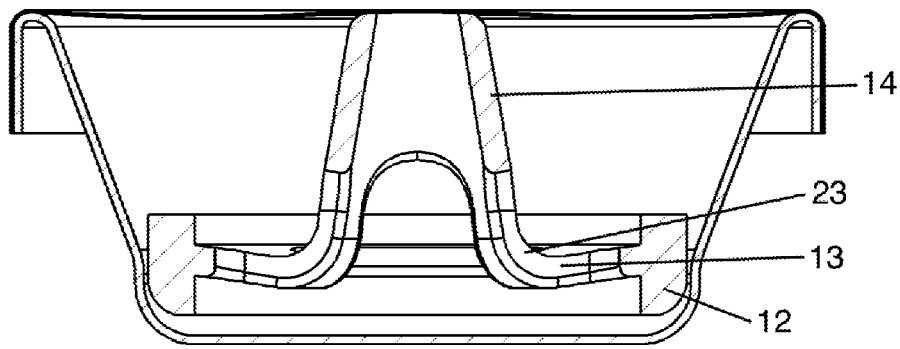
FIG. 5B is a view that shows the collapsed piercing device.
Figure 6:
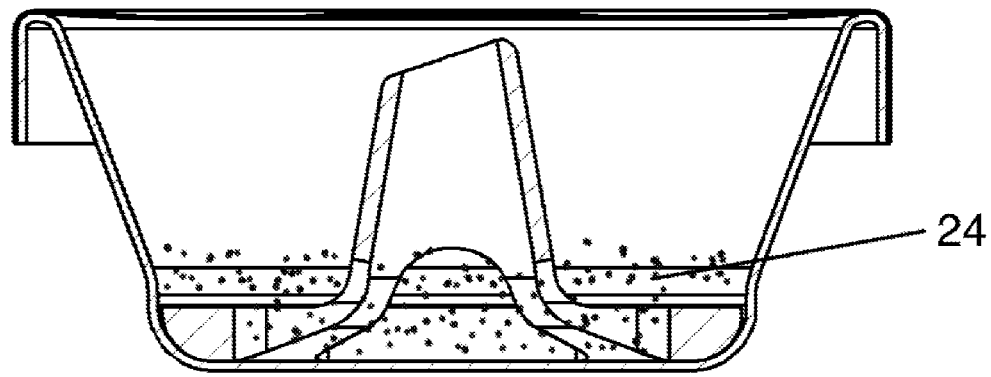
FIG. 6 is a view of a dosage form with internal piercing device loaded with dry powder.
Figure 7:
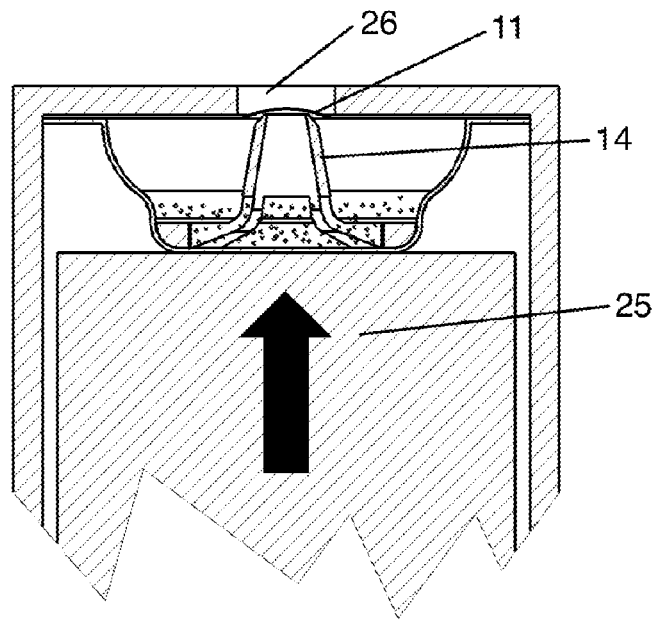
FIG. 7 demonstrates a dosage form during the pressurization phase.
Figure 8:
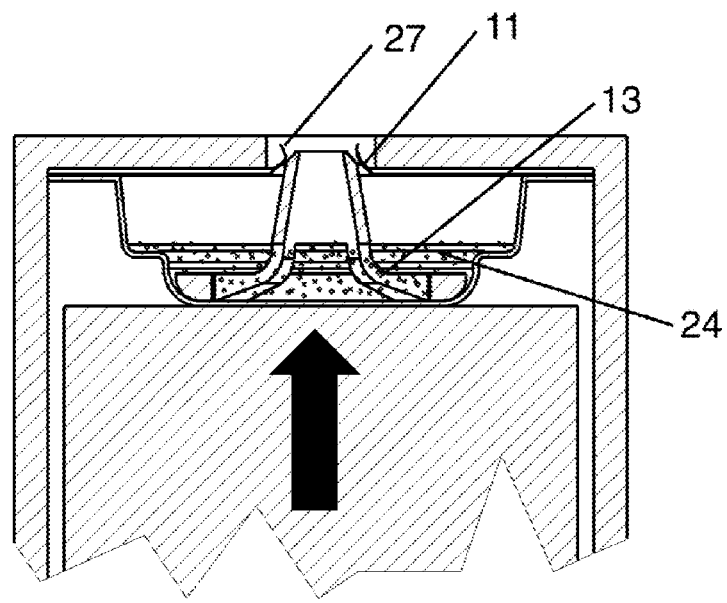
FIG. 8 demonstrates a dosage form during the piercing phase.
Figure 9:
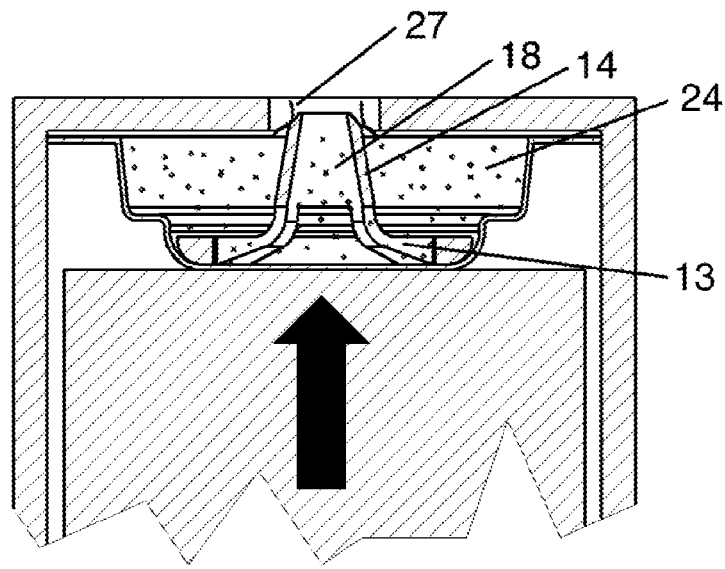
FIG. 9 demonstrates a dosage form during the agitation and break up phase.
Figure 10:
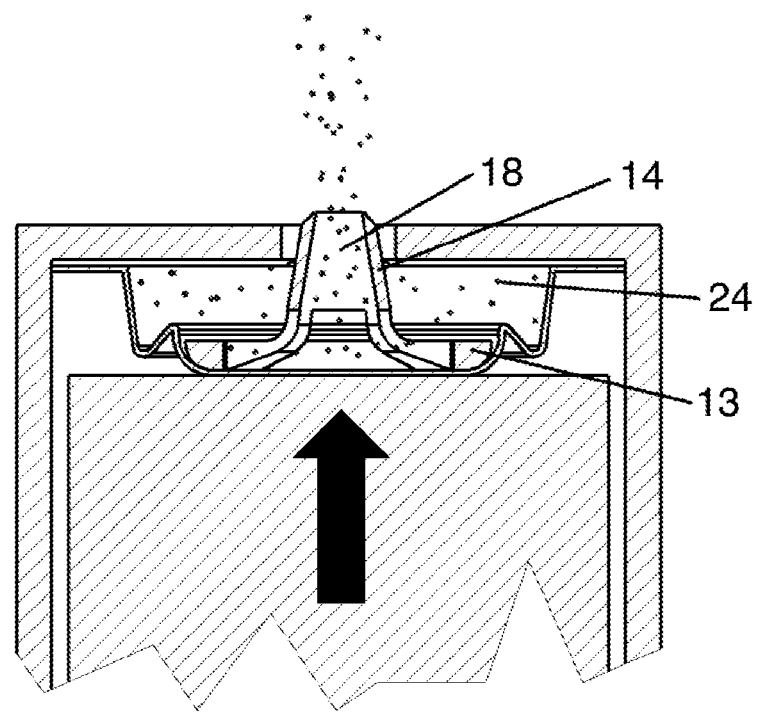
FIG. 10 demonstrates a dosage form during the dispense phase.

An embodiment of internal piercing device is shown in FIGS. 5A and 5B whereby the legs 13 or members connecting a ring base 12 to the hollow elongated tip 14 are designed with a narrowed section 23 such that during blister crush and prior to piercing, the tip collapses into the disk. The arched connecting members invert themselves which snaps the lower ring forward or upward (FIG. 5B). In this embodiment, the internal piercing device acts as a mechanical energy storage device that imparts energy into the dosage form prior to and during dispense to agitate and disperse the powder.

There are multiple stages involved in a typical powder dispense from a dosage form. They can be generally described as phases, all of which interact and can overlap one another. They start with an actuation by a force external to the blister acting upon a rod, cam, lever, or other means, mechanical or electromechanical, known in the art, to result in crushing of the blister form, which causes a pressurization of the sealed dosage form, which promotes the agitation and breakup of the powder. This phase overlaps substantially with the piercing phase, whereby the internal piercing device is moved forward or upward during crushing and punctures or pierces the lidstock from the inside. Once pierced, the pressure equalization and dispense phases begin.

FIGS. 6-10 illustrates the sequence of dispense phases. FIG. 6 shows a blister dosage form containing the internal piercing device as was previously shown in FIG. 3 loaded with powder 24 as stored. FIG. 7 shows the dosage form loaded into a dispensing device. As the plunger 25 compresses the blister, the piercing device stretches the lidstock 11 prior to piercing. FIG. 7 shows the unit dose blister during pressurization, which occurs up to the point of first fissure of the lidstock 11. The emerging hollow elongated tip 14 then protrudes into the device opening 26. Once fissure of the lidstock occurs 27, FIG. 8, the blister contents 24 are exposed to a pressure gradient between the blister interior and the outside ambient pressure. As the pressure gradient seeks to equilibrate, the turbulent forces within the blister act upon the powder and the piercing device's connecting members which impart irregular velocity vectors to agitate, break up, and disperse the powder 24 (FIG. 9). With the powder broken up by the agitation acting in conjunction with the connecting members 13, the free flowing powder is propelled into the center channel 18 of the elongated hollow tip 14 and exits the blister and delivered to the user, as shown in FIG. 10.

When the dose is to be administered, the dosage form is placed in a device designed to administer the pharmaceutical agent to a particular location, such as in the eye, ear, nose, mouth, lungs or skin of a user, for example. The device may administer the pharmaceutical agent through oral, peroral, enteral, parenteral, pulmonary, rectal, otic, topical, nasal, vaginal, lingual, direct injection, intravenous, intraarterial, intracardial, intradermal, intramuscular, intraperitoneal, intracutaneous, intraocular, ophthalmic, intranasal, intrapleural, intrathecal, intratumor, intrauterine, orthotopic, transdermal, buccal, and subcutaneous or other routes of delivery. Many such devices include a firing mechanism that drives a ram against the dosage form with an explosive or incremental force. Examples of such devices are described in pending U.S. Application Publication No. 2008/0177246, incorporated herein in its entirety by reference. In certain embodiments in using the dosage forms of the present invention containing the internal piercing device, the energy input is the result of the hand force supplied by the user. Though additional external energy sources and mechanisms are contemplated herein, the present disclosure provides a device which results in powder agitation and dispersion that occur from internal blister forces provided by the internal piercing device acting in conjunction with the blister pressurization. Said pressurization can in preferred embodiments occur from hand forces supplied to the device by the user. Therefore as compared to existing devices which are generally classified as either active or passive, the present invention is a hybrid of the two whereby the energy required to disperse and deliver the powder to a user is accomplished as a result of the work input provided by the device user and can be augmented by user inspiratory airflow.

Typically, a user administers a dry powder orally, intranasally or topically via a hand levered device that contains one or more dosage forms of the present invention. It is an advantage of the present disclosure that the dosage form can be incorporated into a multitude of devices and configurations. Further, the internal piercing devices and dosage forms can operate independent of orientation, either horizontally, vertically, or at an angle.

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

The invention claimed is:

1. A piercing device internal to a dosage form for dispensing a predetermined quantity of dry powder to a user, said device comprising:

a base comprised of a ring containing no ports;

a hollow elongated member comprising an internal channel and a piercing tip;

one or more legs or members providing support to the hollow elongated member and connecting it to the base;

wherein a flow path is formed to allow communication of the dosage form contents between the support members and into the hollow elongated member without the use of base ports.

2. The piercing device of claim 1, wherein the support members are shaped as substantially flat elements or ribs.

3. The piercing device of claim 1, wherein the support members are curved, angled, or arched effective to form a substantially conical or concave shape region at the base of the hollow elongated member.

4. The piercing device of claim 1, wherein the support members have thin, narrowed, scored, or pinched sections, or otherwise designed such that the piercing device bends, springs, vibrates or collapses during crushing of the blister to affect a mechanical release of energy prior to and/or during dispense.

5. The piercing device of claim 1, wherein the elongated hollow member is in communication with a mesh or porous base.

6. A dosage form containing an internal piercing device of claim 1 and a composition formulated as a dry powder for administration to a human or nonhuman animal.

7. A device for dispensing a predetermined quantity of dry powder to a user, comprising:
- a body comprising a nozzle end designed for insertion into a nostril of a user;
- a trigger device;
- a dosage form comprising a crushable ampoule or blister comprising an internal volume, a pierceable membrane and containing the powder and the piercing mechanism within the internal volume;
- wherein the internal piercing device comprises a base comprised of a ring containing no ports;
- a hollow elongated member comprising an internal channel and a piercing tip;
- one or more legs or members providing support to said hollow elongated member and connecting it to the base;
- wherein a flow path is formed to allow communication of the dosage form contents between the support members and into the hollow elongated member without the use of base ports;
- an actuator in contact with the trigger device;
- a plunger connected to the actuator; and
- wherein operating the trigger causes the plunger to crush the dosage form and the piercing device to penetrate the pierceable membrane and discharge the powder through the discharge channel;
- and further wherein the actuator modifies a mechanical force applied from the trigger device to the plunger.

8. The device of claim 7, wherein the internal piercing device further comprises support members that are shaped as substantially flat elements or ribs.

9. The device of claim 7, wherein the internal piercing device further comprises support members that are curved, angled, or arched effective to form a substantially conical or concave shaped region at the base of the hollow elongated tip.

10. The device of claim 7, wherein the internal piercing device further comprises support members that have thin, narrowed, scored, or pinched sections, or otherwise designed such that the piercing device bends, springs, vibrates or collapses during crushing of the blister to affect a mechanical release of energy prior to and/or during dispense.

11. The device of claim 7, wherein the internal piercing device further comprises an elongated hollow member in communication with a mesh or porous base.

* * * * *